United States Patent [19]

Takashima et al.

[11] Patent Number: 5,395,758
[45] Date of Patent: Mar. 7, 1995

[54] PROCESS FOR PRODUCTION OF AMIDE COMPOUNDS USING AGROBACTERIUM RADIOBACTER

[75] Inventors: Yoshiki Takashima, Minoo; Kazuo Kumagai, Sanda; Satoshi Mitsuda, Takarazuka, all of Japan

[73] Assignee: Sumitomo Chemical Company, Limited, Osaka, Japan

[21] Appl. No.: 54,250

[22] Filed: Apr. 30, 1993

[30] Foreign Application Priority Data

Apr. 30, 1992 [JP] Japan .................................. 4-111265

[51] Int. Cl.⁶ ...................... C12P 13/00; C12P 13/02; C12P 17/12; C12N 1/20
[52] U.S. Cl. .................................. 435/122; 435/128; 435/129; 435/170; 435/228; 435/252.5
[58] Field of Search ............... 435/128, 129, 170, 228, 435/122, 252.5

[56] References Cited

U.S. PATENT DOCUMENTS

| | | | |
|---|---|---|---|
| 4,001,081 | 1/1977 | Commeyras et al. | 195/29 |
| 4,248,968 | 2/1981 | Watanabe et al. | 435/129 |
| 4,555,487 | 11/1985 | Yamada et al. | 435/253 |
| 4,637,982 | 1/1987 | Yamada et al. | 435/129 |
| 4,800,162 | 1/1989 | Matson | 435/280 |
| 5,089,411 | 2/1992 | Yamada et al. | 435/244 |

FOREIGN PATENT DOCUMENTS

| | | |
|---|---|---|
| 0530522A2 | 10/1993 | European Pat. Off. . |
| 58-86093 | 5/1983 | Japan . |
| 61-162193 | 7/1986 | Japan . |
| 64-86889 | 3/1989 | Japan . |
| 04197189 | 7/1992 | Japan . |
| 0515384 | 1/1993 | Japan . |
| 0530982 | 2/1993 | Japan . |
| 0530983 | 2/1993 | Japan . |
| 0530984 | 2/1993 | Japan . |

OTHER PUBLICATIONS

Agric. Biol. Chem., 51(12), 3193–3199, 1987, Screening, Isolation and Taxonomical Properties of Microorganisms. . . .

Primary Examiner—Douglas W. Robinson
Assistant Examiner—Deborah K. Ware
Attorney, Agent, or Firm—Birch, Stewart, Kolasch & Birch

[57] ABSTRACT

There is disclosed a process for production of amide compounds which includes converting a nitrile compound into an amide compound using a cultured broth of bacterial cells, or bacterial cells or materials obtainable by treating bacterial cells, the bacterial cells being cells of a microorganism *Agrobacterium radiobacter* FERM BP-3843, having activity to convert nitrile compounds into corresponding amide compounds.

8 Claims, No Drawings

PROCESS FOR PRODUCTION OF AMIDE COMPOUNDS USING AGROBACTERIUM RADIOBACTER

FIELD OF THE INVENTION

The present invention relates to a process for production of amide compounds and microorganisms for use in this process.

BACKGROUND OF THE INVENTION

In recent years, biological catalysts such as microorganisms have been largely utilized for chemical reactions. For example, it is well known that nitrile compounds can be converted into amide compounds using a specific microorganism.

Examples of the process for such conversion are those which utilize a microorganism of the genus such as Bacillus, Bacteridium, Micrococcus or Brevibacterium (U.S. Pat. No. 4,001,081); Corynebacterium or Nocardia (U.S. Pat. No. 4,248,968); Pseudomonas (U.S. Pat. No. 4,555,487); Rhodococcus or Microbacterium (European Patent Application No. 188316 (laid open)); and Fusarium (Japanese Patent Laid-open Publication No. 86889/1989).

As described above, there are known some kinds of microorganisms having activity to convert nitrile compounds into amide compounds; it is, however, required to develop an improved process for production of amide compounds using a microorganism with improved efficiency.

SUMMARY OF THE INVENTION

Under these circumstances, the present inventors have widely searched the nature for microorganisms having higher activity to convert nitrile compounds into amide compounds. As the result, they have found that a microorganism of the genus Agrobacterium, isolated from the soil at a certain place of Kyoto prefecture, has higher activity to hydrate the nitrile groups of nitrile compounds and can convert the nitrile compounds into amide compounds with high efficiency, thereby completing the present invention.

That is, the present invention provides a process for production of an amide compound, characterized in that a nitrile compound is converted into an amide compound using a microorganism of the genus Agrobacterium, having activity to convert nitrile compounds into amide compounds, in the form of a cultured broth of its bacterial cells, its bacterial cells, or materials obtainable by treating its bacterial cells.

The present invention also provides a microorganism for use in this process, including any mutant thereof.

DETAILED DESCRIPTION OF THE INVENTION

According to the process of the present invention, various nitrile compounds can be converted into amide compounds. Examples of the nitrile compound are aliphatic nitriles such as n-butyronitrile, n-valeronitrile, isobutyronitrile, acetonitrile and pivalonitrile, etc.; nitrile compounds containing one or more halogen atoms, such as 2-chloropropionitrile, etc.; unsaturated aliphatic nitrile compounds such as acrylonitrile, crotononitrile and methacrylonitrile, etc.; hydroxynitrile compounds such as lactonitrile and mandelonitrile, etc.; aminonitrile compounds such as 2-phenylglycinonitrile, etc.; aromatic nitrile compounds such as benzonitrile and cyanopyridines, etc.; and dinitrile compounds such as malononitrile, succinonitrile and adiponitrile, etc. Preferred are n-butyronitrile, n-valeronitrile, isobutyronitrile, acetonitrile, pivalonitrile, 2-chloropropionitrile, acrylonitrile, crotononitrile, methacrylonitrile, benzonitrile, 2-cyanopyridine, 3-cyanopyridine, 4-cyanopyridine, malononitrile, succinonitrile and adiponitrile.

The conversion of nitrile compounds into amide compounds is achieved by use of a microorganism of the genus Agrobacterium, having activity to convert nitrile compounds into amide compounds. Among the microorganisms of the genus Agrobacterium, preferred is *Agrobacterium radiobacter* SC-C15-1, which has been found by the present inventors to have higher activity to hydrate the nitrile groups of nitrile compounds and deposited with the Fermentation Research Institute (renamed "National Institute of Bioscience and Human Technology") in the Agency of Industrial Science and Technology, under the accession number of FERM BP-3843 on Apr. 23, 1992, under the Budapest Treaty.

The following will describe the bacteriological characteristics of *Agrobacterium radiobacter* SC-C15-1.

(a) Morphology
1. Shape and size of cells Shape: rods Size: $0.5$–$0.8 \times 0.8$–$2$ $\mu$m
2. Polymorphism: none
3. Motility: active, peritrichous flagella
4. Sporulation: none
5. Gram staining: negative
6. Acid fastness: none (b) Growth properties
1. Broth agar plate culture: round, convex, no glossy, pale brown
2. Broth agar slant culture: no glossy, pale brown
3. Broth liquid culture: uniform turbid growth
4. Broth gelatin stab culture: not liquefied
5. Litmus milk: slightly coagulated (c) Physiological properties:
1. Nitrate reduction: +
2. Denitrification: ± ~ +
3. MR test: −
4. VP test: +
5. Indole formation: −
6. Hydrogen sulfide formation: +
7. Starch hydrolysis: −
8. Citrate utilization
   Koser medium: +
   Christensen medium: +
9. Inorganic nitrogen source utilization
   $NaNO_3$: +
   $(NH_4)_2SO_4$: +
10. Pigment formation
    King A medium: −
    King B medium: −
11. Urease: +
12. Oxydase: +
13. Catalase: +
14. Growth conditions
    pH: 6.2–9.6
    Temp.: 4°–39° C.
15. Attitude to oxygen: aerobic
16. O-F test: O
17. Acid and gas formation from sugar

|  | Acid | Gas |
|---|---|---|
| L-Arabinose: | + | − |

-continued

|  | Acid | Gas |
|---|---|---|
| D-Xylose: | + | − |
| D-Glucose: | + | − |
| D-Mannose: | + | − |
| D-Fructose: | + | − |
| D-Galactose: | + | − |
| Maltose: | + | − |
| Sucrose: | + | − |
| Lactose: | + | − |
| Trehalose: | + | − |
| D-Sorbitol: | + | − |
| D-Mannitol: | + | − |
| Inositol: | ± | − |
| Glycerol: | + | − |
| Starch: | − | − |

(d) Other properties

1. Poly($\beta$-hydroxybutyric acid) accumulation: −
2. Algininedihydrase: +
3. GC content: 58.7%

These characteristics were compared with the data disclosed in "Bergey's Manual of Systematic Bacteriology" (1984), and the microorganism found by the present inventors was identified as *Agrobacterium radiobacter*.

It should be noted that there have not yet been known any microorganism of the genus Agrobacterium, having activity to convert nitrile compounds into amide compounds. In this respect, the microorganism of the present invention, *Agrobacterium radiobacter* SC-C15-1, is considered to be a novel strain. In addition, any variant of this strain, i.e., any mutant derived from *Agrobacterium radiobacter* SC-C15-1, any cell fusion strain or any recombinant strain is also available for the process of the present invention.

A culture of the microorganism for use in the process of the present invention can be prepared on various kinds of media containing carbon and nitrogen sources, organic and/or inorganic salts, and the like, all of which have been widely used for preparing a culture of ordinary bacteria.

Examples of the carbon source are glucose, glycerol, dextrin, sucrose, animal and vegetable oils, molasses, etc. Examples of the nitrogen source are organic and inorganic nitrogen sources such as broth, peptone, yeast extract, malt extract, soy bean powder, corn steep liquor, cotton seed powder, dry yeast, casamino acid, ammonium chloride, sodium nitrate, ammonium nitrate, ammonium sulfate, ammonium acetate and urea, etc.

Examples of the organic and inorganic salts are chlorides, sulfates, acetates, carbonates and phosphates of elements such as potassium, sodium, calcium, magnesium, iron, manganese, cobalt, copper and zinc, etc. Specific examples thereof are potassium chloride, sodium chloride, magnesium sulfate, ferrous sulfate, manganese sulfate, cobalt chloride, zinc sulfate, copper sulfate, sodium acetate, calcium carbonate, sodium carbonate, potassium monohydrogenphosphate, potassium dihydrogenphosphate, sodium monohydrogenphosphate and sodium dihydrogenphosphate.

In the process of the present invention, it is preferred that a nitrile compound such as isovaleronitrile and crotononitrile, or an amide compound such as crotonamide, is added to the culture medium for the purpose of enhancing the activity to hydrate nitrile groups, of the microorganism used therein. For example, these compounds may be used at an amount of from about 10 mg to about 1 g per 100 mL of the culture medium.

A culture of the microorganism for use in the process of the present invention is prepared according to conventional procedures employed for ordinary bacteria, in the form of either a solid culture or a liquid culture such as a shaking culture using test tubes, reciprocating shakers or rotary shakers, and other cultures using jar fermenters or fermentation tanks, etc.

A culture of the microorganism is usually incubated under aerobic conditions. In particular, when a jar fermenter or a fermentation tank is used, it is necessary to introduce aseptic air thereinto, usually at a rate of from about 0.1 to about 2 times the culture volume per minute.

The incubation temperature may vary within a range in which the microorganism used is viable in culture. For example, the culture is incubated at a temperature of from about 20° to about 40° C., preferably from about 25° to about 35° C. Preferably, the medium pH is controlled at from about 6 to about 8.

The incubation period may vary, depending upon various conditions, and it is usually preferred that the culture is incubated over a period of from about 1 to about 7 days.

The process of the present invention is conducted, for example, as follows.

The cultured broth of the bacterial cells, the bacterial cells, or the materials obtainable by treating the bacterial cells of the microorganism prepared in the manner as described above are suspended in water or an aqueous solution such as a phosphate buffer, and this suspension is reacted with a nitrile compound.

As used herein, "materials obtainable by treating bacterial cells" refers to disrupted bacterial cells or enzymes contained therein, obtained by a conventional technique such as ultrasonic disintegration, homogenization or disruption with a French press, or referred to immobilized preparations obtainable by immobilizing untreated or disrupted bacterial cells, or enzymes contained therein, in a readily removable state after their insolubilization, according to an immobilization method such as a carrier-supporting method in which these materials are supported on an appropriate carrier through covalent linkage, ionic bonding, adsorption or the like, or an inclusion method in which these materials are included in the network structure of a polymer.

The bacterial cells or the materials obtainable by treating the bacterial cells are usually used at a concentration of from about 0.01 to about 20 wt %, preferably from about 0.01 to about 10 wt %. In the case of enzymes or immobilized preparations, the concentration thereof may vary depending upon their purity or immobilization method used; for example, it is preferred that the enzymes and immobilized preparation are prepared so as to have activity to hydrate nitrile groups similar to that of the bacterial cells or the materials obtainable by treating the bacterial cells. The cultured broth of the bacterial cells may be used without any further treatment before addition of a nitrile compound. It is preferred that the cultured broth of the bacterial cells is diluted or concentrated so as to have activity to hydrate nitrile groups similar to that of the bacterial cells or the material obtainable by treating the bacterial cells.

The reaction is usually carried out at a temperature of from about 0° to about 50° C., preferably from about 0° to about 30° C., at a pH of from about 6 to about 10, preferably from about 7 to about 9, for a period of from about 10 minutes to about 48 hours. When the pH is controlled within the above range, the bacterial cells can accumulate the resulting amide compound into the reaction mixture at high concentrations.

The resulting amide compound can be recovered from the reaction mixture by any conventional method known in the art. For example, the bacterial cells or the materials obtainable by treating the bacterial cells are separated from the reaction mixture by centrifugation, etc., followed by treatment with activated charcoal or an ion exchange resin to remove impurities. The purified mixture is concentrated by distillation or evaporation under reduced pressure, and the precipitated crystals are recrystallized from an organic solvent such as methanol, etc., to give the desired amide compound.

The present invention will be further illustrated by way of the following examples which are not to be construed to limit the scope thereof.

EXAMPLE 1

(Isolation of Bacterial Cells)

At a certain place of Kyoto prefecture, soil was collected, and added to a culture medium (pH 7.0) containing potassium phosphate (0.3 wt %), dipotassium phosphate (0.7 wt %), glucose (0.2 wt %), sodium citrate (0.05 wt %), magnesium sulfate (0.01 wt %), ferrous sulfate (0.005 wt %), manganese sulfate (0.005 wt %), cobalt chloride (0.005 wt %), zinc sulfate (0.005 wt %), vitamines (very small amounts) and various nitrile compounds (0.05–0.5 wt %), followed by shaking culture using a reciprocating shaker at 30° C. for 21 days. A part of this cultured broth was spread on an agar medium containing the same ingredients as described above. The culture was incubated to form some colonies, from which a certain strain was screened for the presence of activity to hydrate nitrile groups. Thus, *Agrobacterium radiobacter* SC-C15-1 was obtained as a bacterial strain having higher activity to hydrate nitrile groups.

EXAMPLE 2

(Cultured Broth of Bacterial Cells)

In a 500-mL Sakaguchi flask, placed was a sterilized culture medium (100 mL, pH 7.2) containing glycerol (1.0 wt %), polypeptone (0.5 wt %), yeast extract (0.3 wt %), malt extract (0.3 wt %), isovaleronitrile (0.1 wt %), ferrous sulfate (0.001 wt %), manganese sulfate (0.001 wt %), cobalt chloride (0.001 wt %) and zinc sulfate (0.001 wt %). This flask was inoculated with a cultured broth (1 mL) of *Agrobacterium radiobacter* SC-C15-1 which had been incubated on the same culture medium as described above. This flask was incubated at 30° C. with reciprocal shaking at a rate of 135 stroke/min. for 2 days, resulting in a cultured broth of bacterial cells.

EXAMPLE 3

(Reaction No. 1)

To the cultured broth of bacterial cells (50 mL) obtained in Example 2, acrylonitrile (1.11 g, 21.0 mmol) was added, and the reaction was allowed to proceed at 20° C. while stirring with a magnetic stirrer. Three hours after the initiation of the reaction, an aliquot (1.0 mL) of the reaction mixture was taken, and the reaction was stopped by addition of 2N HCl (0.1 mL) to this aliquot. The reaction mixture was analyzed by gas chromatography under the conditions described below. As the result of this analysis, all the portions of acrylonitrile added were entirely converted into acrylamide, and there was found no by-product such as acrylic acid.

Conditions for gas chromatography
Column: packed column
Carrier: Porapak type Q (mesh 80–100)
Length: 1.1 m
Column temperature: 210° C.
Flow rate of carrier gas: 50 mL/min
Injection volume of sample: 2 $\mu$L

EXAMPLE 4

(Reaction No. 2)

From the cultured broth (100 mL) of bacterial cells of *Agrobacterium radiobacter* SC-C15-1 obtained in Example 2, bacterial cells were collected by centrifugation (10,000×g, 10 min.). The collected bacterial cells were washed with 0.05M phosphate buffer (pH 7.7), and suspended in the same buffer (50 mL) as that used for washing. To this suspension, acrylonitrile (6.62 g, 125 mmol) was added in three portions in such a manner that its concentration did not exceed 5 wt %. The reaction was allowed to proceed at 20° C. while stirring with a magnetic stirrer. Twenty three hours after the initiation of the reaction, an aliquot (1.0 mL) of the reaction mixture was taken, and the reaction was stopped by addition of 2N HCl (0.1 mL) to this aliquot. The reaction mixture was analyzed by gas chromatography under the same conditions as described in Example 3. As the result of the analysis, all the portions of acrylonitrile added were entirely converted into acrylamide, and there was found no by-product such as acrylic acid.

EXAMPLE 5

(Recovery)

From the reaction mixture obtained in Example 4, bacterial cells were removed by centrifugation (10,000×g, 10 min.). The supernatant was concentrated by distillation at a temperature below 50° C., and the precipitated crystals were recrystallized from methanol to give the desired amide compound (8.2 g, 115 mmol; yield, 92%) as colorless plate crystals. These crystals were confirmed as acrylamide by measurement of its melting point, elemental analysis, IR spectroscopy and NMR spectroscopy.

EXAMPLE 6

(Preparation of Crude Enzyme Solution)

From the cultured broth (8 L) of bacterial cells of *Agrobacterium radiobacter* SC-C15-1 obtained in Example 2, bacterial cells were collected by centrifugation (10,000× g, 10 min.). After washing, these bacterial cells were suspended in 0.05M HEPES-KOH buffer (300 mL, pH 7.2), and disrupted two times with a French press (20,000 psi). The disrupted cells were centrifuged (10,000×g, 30 min.) to remove the residual bacterial cells. Using a dialysis tubing (Wako Pure Chemical Industries, Ltd.), the supernatant was dialyzed against four changes of 10 mM HEPES-KOH buffer (pH 7.2) at 4° C. for 24 hours. The dialysate was allowed to pass through a column (50 mm$\phi$×200 mm) of DEAE-Sepharose FF (Pharmacia) as an anion exchange resin, previously equilibrated with 0.05M HEPES-KOH buffer (pH 7.2), thereby effecting adsorption of enzymes thereon.

Then, 0.05M HEPES-KOH buffer (pH 7.2) was allowed to pass through the column for washing, and elution was effected by a gradient of 0.05M HEPES-KOH buffer (pH 7.2) containing 0M to 1.0M potassium chloride. The fraction exhibiting the activity to hydrate nitrile groups was recovered and dialyzed, using a dialysis tubing (Wako Pure Chemical Industries, Ltd.), against four changes of 10 mM HEPES-KOH buffer (pH 7.2) at 4° C. for 24 hours. The dialysate was purified by anion exchange chromatography under the same conditions as described above, except that elution was effected by a gradient of 0.05 mM HEPES-KOH buffer (pH 7.2) containing 0.2M to 0.8M potassium chloride. The eluent was dialyzed in the same manner as described above, resulting in a crude enzyme solution.

The activity to hydrate nitrile groups was determined as follows.

A sample of the crude enzyme solution (1 mL) was added to 100 mM aqueous propionitrile (9 mL, pH 7.7), and the reaction was allowed to proceed at 10° C. After ten minutes, the reaction was stopped by addition of 2N HCl (1 mL). An aliquot of the reaction mixture was analyzed by gas chromatography to determine the amount of propionamide produced.

As used hereinbelow, with respect to the unit of enzyme activity, the activity to convert 1 μmol of propionitrile into propionamide per minute was defined as 1 unit (U).

EXAMPLE 7

(Reaction No. 3)

In this example, nitrile-hydrating enzymes contained in *Agrobacterium radiobacter* SC-C15-1 were examined for the ability to convert various nitrile compounds into the corresponding amide compounds. To the crude enzyme solution (50 U) obtained in Example 6, added were 0.05M phosphate buffer (10 mL, pH 7.7) and each (1 mmol) of the tested nitrile compounds shown in Table 1 as a substrate, and the reaction was allowed to proceed at 30° C. for 1 hour. As the result, it was found that the nitrile-hydrating enzymes contained in *Agrobacterium radiobacter* SC-C15-1 had the ability to convert all the tested nitrile compounds into the corresponding amide compounds and the conversion rate was 100% in all cases. The reaction solution was analyzed by gas chromatography or liquid chromatography to determine the amount of amide compound produced or the amount of nitrile compound consumed.

TABLE 1

| Tested nitrile compound | Conversion rate (%) |
| --- | --- |
| n-Butyronitrile | 100 |
| n-Valeronitrile | 100 |
| Isobutyronitrile | 100 |
| 2-Chloropropionitrile | 100 |
| Acrylonitrile | 100 |
| Crotononitrile | 100 |
| 3-Cyanonitrile | 100 |
| 4-Cyanonitrile | 100 |
| Malononitrile | 100 |
| Succinonitrile | 100 |
| Adiponitrile | 100 |

EXAMPLE 8

(Reaction No. 4)

In this example, nitrile-hydrating enzymes contained in *Agrobacterium radiobacter* SC-C15-1 were examined for the ability to convert the tested nitrile compounds (shown in Table 2) other than those tested in Example 7, into the corresponding amide compounds. To the crude enzyme solution (60 U) obtained in Example 6, added were 0.05M phosphate buffer (20 mL, pH 7.7) and each (1 mmol) of the tested nitrile compounds shown in Table 2 as a substrate, and the reaction was allowed to proceed at 30° C. for 3 hours. As the result, it was found that the nitrile-hydrating enzymes contained in *Agrobacterium radiobacter* SC-C15-1 had the ability to convert all the tested nitrile compounds into the corresponding amide compounds and the conversion rate was 100% in all cases. The reaction solution was analyzed by gas chromatography or liquid chromatography to determine the amount of amide compound produced or the amount of nitrile compound consumed.

TABLE 2

| Tested nitrile compound | Conversion rate (%) |
| --- | --- |
| Acetonitrile | 100 |
| Pivalonitrile | 100 |
| Methacrylonitrile | 100 |
| Benzonitrile | 100 |
| 2-Cyanonitrile | 100 |

As described above, the present invention makes it possible to produce amide compounds with high purity by hydrating the nitrile groups of nitrile compounds at ordinary temperatures under normal pressures and then converting into the corresponding amide compounds, with the use of a microorganism of the genus Agrobacterium.

What is claimed is:

1. A process for production of amide compounds which comprises converting a nitrile compound into a corresponding amide compound by hydrating said nitrile compound in the presence of a cultured broth of bacterial cells, intact bacterial cells, disrupted bacterial cells or enzymes contained therein, or immobilized preparations obtainable by immobilizing intact bacterial cells, disrupted bacterial cells or enzymes contained therein, said bacterial cells being cells of a biologically pure culture of *Agrobacterium radiobacter* FERM BP-3843, wherein the nitrile compound is selected from the group consisting of aliphatic nitrile compounds, nitrile compounds containing one or more halogen atoms, unsaturated aliphatic nitrile compounds, hydroxynitrile compounds, aminonitrile compounds, aromatic nitrile compounds and dinitrile compounds.

2. A process according to claim 1, wherein the nitrile compound is selected from the group consisting of n-butyronitrile, n-valeronitrile, isobutyronitrile, acetonitrile, pyvalonitrile, 2-chloropropionitrile, acrylonitrile, crotononitrile, methacrylonitrile, benzonitrile, 2-cyanopyridine, 3-cyanopyridine, 4-cyanopyridine, malononitrile, succinonitrile and adiponitrile.

3. A biologically pure culture of *Agrobacterium radiobacter* FERM BP-3843.

4. The process according to claim 1, wherein the hydrating reaction is carried out at a temperature of from 0° to about 50° C.

5. The process according to claim 1, wherein the hydrating reaction is carried out at a temperature of from 0° to about 30° C.

6. The process according to claim 1, wherein the hydrating reaction is carried out at a pH of from about 6 to about 10.

7. The process according to claim 1, wherein the hydrating reaction is carried out at a pH of from about 7 to about 9.

8. The process according to claim 1, wherein the hydrating reaction is carried out for a period from about 10 minutes to about 48 hours.

* * * * *